United States Patent [19]
Falck-Pedersen et al.

[11] Patent Number: 5,837,511
[45] Date of Patent: Nov. 17, 1998

[54] NON-GROUP C ADENOVIRAL VECTORS

[75] Inventors: Erik S. Falck-Pedersen, Dobbs Ferry, N.Y.; Ronald G. Crystal, Potomac, Md.; Andrea Mastrangeli; Karil Abrahamson, both of New York, N.Y.

[73] Assignee: Cornell Research Foundation, Inc., Ithaca, N.Y.

[21] Appl. No.: 537,402

[22] Filed: Oct. 2, 1995

[51] Int. Cl.$^6$ .......................... C12N 15/00; C12N 15/86
[52] U.S. Cl. .................... 435/172.3; 435/320.1; 435/325; 435/235.1; 514/44
[58] Field of Search .................. 435/320.1, 5, 6, 435/4, 235.1; 514/44; 424/93.1, 93.2, 9

[56] References Cited

U.S. PATENT DOCUMENTS

| | | | |
|---|---|---|---|
| 4,920,209 | 4/1990 | Davis et al. | 435/235 |
| 5,543,328 | 8/1996 | McClelland et al. | 435/320.1 |

FOREIGN PATENT DOCUMENTS

| | | |
|---|---|---|
| 0 638 316 | 2/1995 | European Pat. Off. |
| WO 94/28152 | 12/1994 | WIPO |

OTHER PUBLICATIONS

Kremer et al, Adenovirus and adeno–associated virus mediated gene transfer, British Medical Bulletin, vol. 51, No. 1, pp. 31–44, 1995.

Jolly, Douglas, Viral Vector systems for Gene Therapy, Cancer Gene Therapy, vol. 1, No. 1, pp. 51–64, 1994.

Berkner, K. L., Expression of Heterologous Sequences in Adenoviral Vectors, Current Topics in Microbiology and Immunology, vol. 158 pp. 39–66, Aug. 12, 1992.

Crystal, Ronald G., The Gene as the Drug, Nature Medicine, vol. 1, No. 1, pp. 15–17, Jan. 1995.

Chengalvala et al., *Vaccine*, 9, 485–490 (1991).

Chengalvala et al., *J. Gen. Virol.*, 75, 125–131 (1994).

Horwitz, "Adenoviridae and Their Replication," in *Fundamental Virology* (Fields et al., eds., Raven Press Ltd., New York, NY, 2d ed., 1991), pp. 771–813.

Lindley et al., *Gene*, 138, 165–170 (1994).

Straus, "Adenovirus Infections in Humans," in *Adenoviruses* (Plenum Press, New York, NY 1984), pp. 451–496.

Orkin et al. Report and recommendation of the panel to assess the NIH investment in research on gene therapy. Distributed by the National Institutes of Health, Dec. 7, 1995.

Mastrangeli et al., *J. Clinical Investigation*, 91, 225–234 (1993).

*Primary Examiner*—Jasemine C. Chambers
*Assistant Examiner*—Deborah J. R. Clark
*Attorney, Agent, or Firm*—Leydig, Voit & Mayer, Ltd.

[57] ABSTRACT

The present invention provides replication-deficient non-group C adenoviral vectors. Also provided is a therapeutic method, particularly relating to gene therapy, vaccination, and the like, involving the use of such vectors incorporating a foreign nucleic acid.

17 Claims, 4 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GAGCTCACCG  GTCTCTCTAT  ATAATATACC                                    3 0
```

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

(xi) SEQUENCE DESCRIPTION: SEQ ID NO:2:

TCTAGAGCGG CCGCAGCGAT CAGCTGACAC CTACG                35

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCTAGCGTCG ACGAAGAAAT GCATGTTTG                29

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGGCCCGGTA CCCAATGATC GAAACCG                27

NON-GROUP C ADENOVIRAL VECTORS

TECHNICAL FIELD OF THE INVENTION

The present invention relates to adenoviral gene transfer vectors which comprise a DNA segment found in non-group C adenoviruses and, typically, a foreign gene for expression within a cell. The present invention also relates to the therapeutic and diagnostic use of such vectors.

BACKGROUND OF THE INVENTION

During the winter and spring of 1952–1953, Rowe and his colleagues at the National Institutes of Health (NIH) obtained and placed in tissue culture adenoids that had been surgically removed from young children in the Washington, D.C. area (Rowe et al., *Proc. Soc. Exp. Biol. Med.*, 84, 570–573 (1953)). After periods of several weeks, many of the cultures began to show progressive degeneration characterized by destruction of epithelial cells. This cytopathic effect could be serially transmitted by filtered culture fluids to established tissue cultures of human cell lines. The cytopathic agent was called the "adenoid degenerating" (Ad) agent. The name "adenovirus" eventually became common for these agents. The discovery of many prototype strains of adenovirus, some of which caused respiratory illnesses, followed these initial discoveries (Rowe et al., supra; Dingle et al., *Am. Rev. Respir. Dis.*, 97, 1–65 (1968); Horwitz, "Adenoviridae and Their Replication," in *Fundamental Virology* (Fields et al., eds., Raven Press Ltd., New York, N.Y., 2d ed., 1991), pp. 771–813).

All adenoviruses are morphologically and structurally similar. These viruses are nonenveloped, regular icosahedrons, 65–80 nm in diameter, consisting of an external capsid and an internal core. The capsid is composed of 20 triangular surfaces or facets and 12 vertices (Horne et al., *J. Mol. Biol.*, 1, 84–86 (1959)). The facets are comprised of hexons and the vertices are comprised of pentons. A fiber projects from each of the vertices. In addition to the hexons, pentons, and fibers, there are eight minor structural polypeptides, the exact positions of the majority of which are unclear.

The viral core contains a linear, double-stranded DNA molecule with inverted terminal repeats (ITRs), which have been noted to vary in length from 103 bp to 163 bp in different isolates (Garon et al., *Proc. Natl. Acad. Sci. USA*, 69, 2391–2394 (1972); Wolfson et al., *Proc. Natl. Acad. Sci. USA*, 69, 3054–3057 (1972); Arrand et al., *J. Mol. Biol.*, 128, 577–594 (1973); Steenberg et al., *Nucleic Acids Res.*, 4, 4371–4389 (1977); Tooze, *DNA Tumor Viruses* (2nd ed., Cold Spring Harbor, N.Y.: Cold Spring Harbor Laboratory, 1981), pp. 943–1054). The ITRs harbor origins of DNA replication (Garon et al., supra; Wolfson et al., supra; Arrand et al., supra; Steenberg et al., supra).

The viral DNA is associated with four polypeptides, namely V, VII, $\mu$, and terminal polypeptide (TP). The 55 kd TP is covalently linked to the 5' ends of the DNA via a dCMP (Rekosh et al., *Cell*, 11, 283–295 (1977); Robinson et al., *Virology*, 56, 54–69 (1973)). The other three polypeptides are noncovalently bound to the DNA and fold it in such a way as to fit it into the small volume of the capsid. The DNA appears to be packaged into a structure similar to cellular nucleosomes as seen from nuclease digestion patterns (Corden et al., *Proc. Natl. Acad. Sci. USA*, 73, 401–404 (1976); Tate et al., *Nucleic Acids Res.*, 6, 2769–2785 (1979); Mirza et al., *Biochim. Biophys. Acta*, 696, 76–86 (1982)).

Beyond the various physical similarities characteristic of the adenoviruses, these viruses have been distinguished into subdivisions with respect to certain criteria, including immunological reactivities, oncogenicity, and GC content of the genome of a given strain. See Horwitz, supra at 777. For example, over 40 serotypes and four hemagglutination groups have been identified among human adenovirus isolates. The following chart summarizes the classification of human adenoviruses, as reviewed by Horwitz, supra at 777:

| Subgroup | Hemagglutination groups | Serotypes | Tumors in animals | Transformation in tissue culture | Percentage of G + C in DNA |
|---|---|---|---|---|---|
| A | IV (little or no agglutination) | 12, 18, 31 | High | + | 48–49 |
| B | I (complete agglutination of monkey erythrocytes) | 3, 7, 11, 14, 16, 21, 34, 35 | Moderate | + | 50–52 |
| C | III (partial agglutination of rat erythrocytes) | 1, 2, 5, 6 | Low or none | + | 57–59 |
| D | II (complete agglutination of rat erythrocytes) | 8, 9, 19, 37, 10, 13, 15, 17, 19, 20, 22–30, 32, 33, 36, 37, 38, 39, 42 | Low or none | + | 57–61 |
| E | III | 4 | Low or none | + | 57–59 |
| F | III | 40, 41 | Unknown | | |

At least with respect to the adenoviral serotypes that have been most studied to date, namely Ad2 and Ad5, which have been fully sequenced, the overall organization of the adenoviral genome is conserved among serotypes such that specific functions are similarly positioned. Portions of other serotypes have been sequenced, the results of which are consistent with the hypothesis of a conserved genetic organization among the adenoviruses. Nevertheless, as is reflected in the chart, the adenoviruses exhibit substantial diversity at the genetic level. For example, viral isolates from the different groups of adenoviruses exhibit variant GC contents in their respective genomes. Moreover, DNA-DNA hybridization studies indicate that there is less than 20% homology between the DNA of different groups, although more refined analysis reveals that conserved sequences can be detected in comparisons of subgenomic segments. For example, in studies of up to 30 map units of DNA length, at least 20–50% of the DNA sequence is noted to vary between groups (Horwitz, supra at 777). In another study, sequences of the origin of replication of subtypes associated with each of the six groups of adenoviruses have been noted to be related but different.

Importantly, albeit unexplained, adenoviruses of different groups do not recombine when co-infection of the same host occurs. In contrast, the adenoviruses recombine efficiently within a group (Sambrook et al., *J. Mol. Biol.*, 97, 369–390 (1975)). The failure of recombination between groups highlights the genetic variance of the adenoviral groups.

The basic physiology of adenoviral infection has been studied predominantly regarding Ad2 and Ad5. According to those studies, adenovirus begins to infect a cell by attachment of the fiber to a specific receptor on the cell membrane (Londberg-Holm et al., *J. Virol.*, 4, 323–338 (1969); Morgan et al., *J. Virol.*, 4, 777–796 (1969); Pastan et al., "Adenovirus entry into cells: some new observations on an old problem," in *Concepts in Viral Pathogenesis*, Notkins et al., eds., Springer-Verlag, New York, N.Y., pp. 141–146 (1987)). Then, the penton base binds to a cellular integrin receptor. The receptor-bound virus then migrates from the plasma membrane to clathrin-coated pits that form endocytic vesicles or receptosomes, where the pH drops to 5.5. The drop in pH is believed to alter the surface configuration of the virus, resulting in receptosome rupture and release of virus into the cytoplasm of the cell.

When the virus reaches the nuclear pores, the viral DNA enters the nucleus, leaving most of the remaining protein behind in the cytoplasm (Philipson et al., *J. Virol.*, 2, 1064–1075 (1968)). However, the viral DNA is not completely protein-free in that at least a portion of the viral DNA is associated with at least four viral polypeptides, namely V, VII, TP and $\mu$, and is converted into a viral DNA-cell histone complex (Tate et al., *Nucleic Acids Res.*, 6, 2769–2785 (1979)).

The cycle from cell infection to production of viral particles lasts 1–2 days and results in the production of up to 10,000 infectious particles per cell (Green et al., *Virology*, 13, 169–176 (1961)). The infection process of adenovirus is divided into early (E) and late (L) phases, which are separated by viral DNA replication, although some events that take place during the early phase also take place during the late phase and vice versa. Further subdivisions of the adenoviral genetic regions have been made to fully describe the temporal expression of viral genes.

During the early phase, viral messenger RNA ("mRNA"), which constitutes a minor proportion of the total RNA present in the cell, is synthesized from both strands of the adenoviral DNA present in the cell nucleus. At least five regions, designated E1, E2, E3, E4, and MLP-L1, are transcribed (Lewis et al., *Cell*, 7, 141–151 (1976); Sharp et al., *Virology*, 75, 442–456 (1976); Sharp, "Adenovirus transcription," in *The Adenoviruses*, Ginsberg, ed., Plenum Press, New York, N.Y., pp. 173–204 (1984)). Each region has at least one distinct promoter and is processed to generate multiple mRNA species.

The products of the early (E) regions (1) serve regulatory roles for the expression of other viral components, (2) are involved in the general shut-off of cellular DNA replication and protein synthesis, and (3) are required for viral DNA replication. The intricate series of events regulating early mRNA transcription begins with expression of certain immediate early regions, including E1A, L1, and the 13.5 kd gene (reviewed in Sharp (1984), supra; Horwitz, supra). Expression of the delayed early regions E1B, E2A, E2B, E3 and E4 is dependent on the E1A gene products. Three promoters—the E2 promoter at 72 map units ("mu"), the protein IX promoter, and the IVa promoter—are enhanced by the onset of DNA replication, but are not dependent on it (Wilson et al., *Virology*, 94, 175–184 (1979)). Their expression characterizes an intermediate phase of viral gene expression. The result of the cascade of early gene expression is the start of viral DNA replication.

Adenoviral DNA replication displaces one parental single-strand by continuous synthesis in the 5' to 3' direction from replication origins at either end of the genome (reviewed in Kelly et al., "Initiation of viral DNA replication," in *Advances in Virus Research*, Maramorosch et al., eds., Academic Press, Inc., San Diego, Calif., 34, 1–42 (1988); Horwitz et al., in *Virology*, Raven Press, New York, 2, 1679–1721 (1990); van der Vliet, "Adenovirus DNA replication in vitro," in *The Eucaryotic Nucleus*, Strauss et al., eds., Telford Press, Caldwell, N.J., 1, 1–29 (1990)). Three viral proteins encoded from E2 are essential for adenoviral DNA synthesis: (1) the single-stranded DNA binding protein (DBP), (2) the adenoviral DNA polymerase (Ad pol), and (3) the pre-terminal protein (pTP). In addition to these essential proteins, in vitro experiments have identified many host cell factors necessary for DNA synthesis.

DNA synthesis is initiated by the covalent attachment of a dCMP molecule to a serine residue of pTP. The pTP-dCMP complex then functions as the primer for Ad pol to elongate. The displaced parental single-strand can form a panhandle structure by base-pairing of the inverted terminal repeats. This terminal duplex structure is identical to the ends of the parental genome and can serve as an origin for the initiation of complementary strand synthesis. Initiation of viral DNA replication appears to be essential for entry into the late phase. The late phase of viral infection is characterized by the production of large amounts of the viral structural polypeptides and the nonstructural proteins involved in capsid assembly. The major late promoter (MLP) becomes fully active and produces transcripts that originate at 16.5 mu and terminate near the end of the genome. Post-transcriptional processing of this long transcript gives rise to five families of late mRNA, designated respectively as L1 to L5 (Shaw et al., *Cell*, 22, 905–916 (1980)). The mechanisms that control the shift from the early to late phase and result in such a dramatic shift in transcriptional utilization are unclear. The requirement for DNA replication may be a cis-property of the DNA template, because late transcription does not occur from a superinfecting virus at a time when late transcription of the primary infecting virus is active (Thomas et al., *Cell*, 22, 523–533 (1980)).

Assembly of the virion is an intricate process from the first step of assembling major structural units from individual polypeptide chains (reviewed in Philipson, "Adenovirus Assembly," in *The Adenoviruses*, Ginsberg, ed., Plenum Press, New York, N.Y. (1984), pp. 309–337; Horwitz, supra). Hexon, penton base, and fiber assemble into trimeric homopolymer forms after synthesis in the cytoplasm. The 100 kd protein appears to function as a scaffolding protein for hexon trimerization and the resulting hexon trimer is called a hexon capsomer. The hexon capsomeres can self-assemble to form the shell of an empty capsid, and the penton base and fiber trimers can combine to form the penton when the components are inside the nucleus. The facet of the icosahedron is made up of three hexon capsomeres, which can be seen by dissociation of the capsid, but the intermediate step of the formation of a group-of-nine hexons has not been observed. Several assembly intermediates have been shown from experiments with temperature-sensitive mutants. The progression of capsid assembly appears dependent on scaffolding proteins, 50 kd and 30 kd. The naked DNA most probably enters the near-completed capsid through an opening at one of the vertices. The last step of the process involves the proteolytic trimming of the precursor polypeptides pVI, pVII, pVIII and pTP, which stabilizes the capsid structure, renders the DNA insensitive to nuclease treatment, and yields a mature virion.

Certain recombinant adenoviral vectors have been used in gene therapy, namely Ad2 and Ad5, both of which are categorized as group C. The use of a recombinant adenoviral vector to transfer one or more recombinant genes enables targeted delivery of the gene or genes to an organ, tissue, or cells in need of treatment, thereby overcoming the delivery problem encountered in most forms of somatic gene therapy. Furthermore, recombinant adenoviral vectors do not require host cell proliferation for expression of adenoviral proteins (Horwitz et al., supra; Berkner, BioTechniques, 6, 616 (1988)). Moreover, if the diseased organ in need of treatment is the lung, use of adenovirus as the vector of genetic information has the added advantage of adenovirus being normally trophic for the respiratory epithelium (Straus, in Adenoviruses, Plenum Press, New York, pp. 451–496 (1984)).

Other advantages of adenoviruses as vectors for human gene therapy include: (i) recombination is rare; (ii) there are no known associations of human malignancies with adenoviral infections despite common human infection with adenoviruses; (iii) the adenoviral genome (which is linear, double-stranded DNA) currently can be manipulated to accommodate foreign genes ranging in size up to 7.0–7.5 kb in length; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz et al., supra; Berkner et al., J. Virol., 61, 1213–1220 (1987); Straus supra; Chanock et al., JAMA, 195, 151 (1966); Haj-Ahmad et al., J. Virol., 57, 267 (1986); Ballay et al., EMBO, 4, 3861 (1985)).

Foreign genes have been inserted into two major regions of the group C adenoviral genome for use as expression vectors, namely the E1 and E3 regions, thus providing singly deficient adenovirus and vectors derived therefrom. Insertion into the E1 region results in defective progeny that require either growth in complementary cells or the presence of an intact helper virus, either of which serves to replace the function of the impaired or absent E1 region (Berkner et al., supra; Davidson et al., J. Virol., 61, 1226–1239 (1987); Mansour et al., Mol. Cell Biol., 6, 2684–2694 (1986)). Currently, there are only a few cell lines that exist that will complement for essential functions missing from a singly deficient adenovirus. Examples of such cell lines include the human embryonic kidney cells known as HEK-293 (Graham et al., Cold Spring Harbor Symp. Quant. Biol., 39, 637–650 (1975)), W162 (Weinberg et al., Proc. Natl. Acad. Sci. USA, 80, 5383–5386 (1983)), and gMDBP (Klessig et al., Mol. Cell. Biol., 4, 1354–1362 (1984); Brough et al., Virology, 190, 624–634 (1992)).

The E1 region of the genome has been used most frequently for expression of foreign nucleic acid. Genes inserted into the E1 region have been placed under the control of various promoters and most produce large amounts of the foreign gene product, dependent on the expression cassette.

The E3 region, the other region noted above as typically used for insertion of foreign nucleic acid, is not essential for virus growth in tissue culture, and the replacement of this region with a foreign nucleic acid expression cassette leads to a virus that can productively grow in a noncomplementing cell line. For example, the insertion and expression of the hepatitis B surface antigen in the E3 region of serotype Ad5 virus with subsequent inoculation and formation of antibodies in the hamster has been reported (Morin et al., Proc. Natl. Acad. Sci. USA, 84, 4626–46 (1987)). Reports of analogous E3 deficiencies created in Ad4 and Ad7 serotypes have also been reported (regarding Ad4, Chengalvala et al., Vaccine, 9, 485–490 (1991); regarding Ad7, Lindley et al., Gene, 138, 165–170 (1994) and Chengalvala et al., J. Gen. Virol., 75, 125–131 (1994)).

In the field of adenoviral gene therapy, clinical studies to date have used only the two aforementioned group C serotypes, namely Ad2 and Ad5. As examples of such studies, see Davidson et al., Nature, 3, 219 (1993), and Mastrangeli et al., J. Clin. Invest., 91, 225–234 (1993). The focus of current studies on the group C serotypes can be understood in view of the fact that the overwhelming majority of basic research studies of characterization of the adenoviruses have been directed to Ad2 and Ad5. See Fields, supra; also see, The Adenoviruses (Ginsberg, ed., Plenum Press, New York, N.Y., (1984). These studies have shown that the group C adenoviruses are exceptionally effective as delivery ehicles for a variety of target tissues, including the respiratory epithelium. See, e.g., Bajocchi et al., Nature Genetics, 3, 229–234 (1993).

There are, however, limitations on the use of group C adenoviral gene therapy vectors. A host can develop an immune response to the particular adenoviral vector being used in gene therapy as a result of natural exposure of the host to the same type of adenovirus prior to the initiation of gene therapy or as a result of the exposure of the host to the adenoviral vector in the course of the gene therapy itself. A cellular immune response can reduce the life span of cells infected with the adenoviral vector and thereby reduce the expression of the foreign nucleic acid, diminishes the overall effectiveness of the gene therapy. Indeed, it has been noted empirically that a major limitation of the currently used group C adenoviral gene therapy systems is the short duration of gene expression obtained thereby. See, e.g., Crystal et al., Nature Genetics, 8, 42–51 (1994). Moreover, a humoral immune response, resulting in the production of antibodies, can significantly reduce the effectiveness of gene therapy using a particular adenoviral vector.

Accordingly, there is a need for additional replication-deficient adenoviral vectors which differ from group C adenoviral vectors. In particular, there is a need for additional replication-deficient adenoviral vectors which allow for the incorporation and expression of foreign nucleic acid and which have physiologies of infection that vary from that of group C adenoviral vectors. The present invention seeks to provide such vectors, as well as methods of using such vectors. These and other objects and advantages of the present invention, as well as additional inventive features, will be apparent from the description of the present invention herein.

BRIEF SUMMARY OF THE INVENTION

The present invention provides an adenoviral gene transfer vector comprising an adenoviral DNA segment, wherein the adenoviral DNA segment is isolated from an adenovirus or is substantially homologous to a DNA segment contained in an adenovirus, wherein the adenovirus is classified as one of group A, B, D, E, or F, and wherein the vector is deficient in at least one region required for viral replication. The present invention also provides methods of using such vectors.

DETAILED DESCRIPTION OF THE INVENTION

Figure 1A:
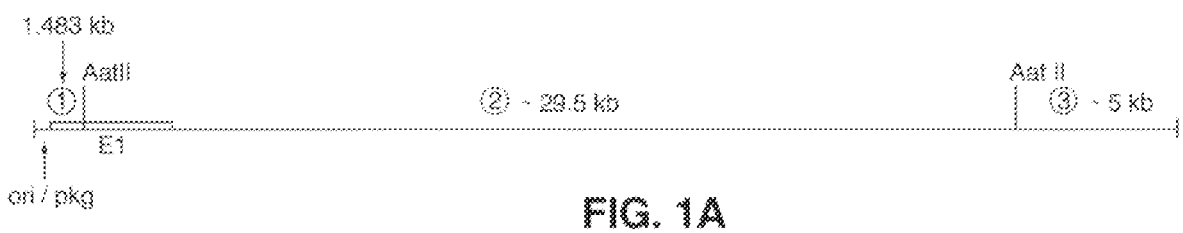
FIG. 1A is a physical map of the Ad7a genome, in which the locations of AatII restriction endonuclease sites are noted.

The present invention is predicated, at least in part, on the discovery that non-group C adenoviruses can be used to prepare replication-deficient adenoviral gene transfer vectors and that such vectors can be propagated in complementing cell lines designed for replication-deficient group C adenoviral vectors. This discovery was unexpected in view of the substantial differences between non-group C adenoviruses and group C adenoviruses, as exemplified by the relatively small amount of similarity between the E1A and E1B gene products of non-group C adenoviruses and group C adenoviruses.

The present invention provides an adenoviral gene transfer vector comprising an adenoviral nucleic acid segment, wherein the adenoviral nucleic acid segment is isolated from an adenovirus or is substantially homologous to a nucleic acid segment contained in an adenovirus, and wherein the adenovirus is a non-group C adenovirus, e.g., an adenovirus of group A, B, D, E, or F. In addition, the adenoviral gene transfer vector of the present invention is replication-deficient, i.e., deficient in at least one region required for viral replication. Typically, the present inventive adenoviral vector will further comprise, generally in place of at least one of the deleted regions required for viral replication, a foreign nucleic acid that encodes a product that has therapeutic and/or prophylactic utility.

The adenoviral classification used in the context of the present invention is that as described above and by Horwitz, supra. As such, a "non-group C adenoviral vector" is based on the serotypic definition, e.g., preferably all of the capsid proteins for such an adenoviral vector originate from a non-group C adenovirus. Thus, the term "non-group C adenoviruses" includes adenoviruses of groups A, B, D, E, and F. Preferred adenoviruses used in the construction of non-group C adenoviral gene transfer vectors of the present invention include Ad12 (group A), Ad7 (group B), Ad30 and Ad36 (group D), Ad4 (group E), and Ad41 (group F). More preferred adenoviruses used in the construction of the non-group C adenoviral gene transfer vectors of the present invention include those of group B, especially Ad7.

Any subtype, mixture of subtypes, or chimeric adenovirus can be used as the source of nucleic acid for the generation of the adenoviral vectors of the present invention, although at least one of the adenoviruses used must be a non-group C adenovirus, and the adenoviral vector must remain a non-group C adenoviral vector as serotypically defined, e.g., such that all of the capsid proteins for such an adenoviral vector originate from a non-group C adenovirus. Thus, for example, a region of a particular non-group C adenovirus, e.g., the E4 region of Ad7, can be replaced with a region of a wild-type group C adenovirus, e.g., the E4 region of Ad2 or Ad5. Such combinations are contemplated to provide a series of recombinant adenoviruses that are immunologically invisible, both with respect to wild-type adenoviruses and currently used adenoviral vectors and those generated in the context of the present invention. Accordingly, a host requiring ongoing gene therapy can be treated using a succession of different adenoviral gene therapy vectors that are not neutralized by antibodies induced in the host in response to earlier natural adenoviral infections and/or earlier gene therapy treatment using other vectors.

While the adenoviral nucleic acid segment which forms part of the present inventive adenoviral vector is preferably isolated from an adenovirus, the adenoviral nucleic acid segment can be also substantially homologous to a nucleic acid segment contained in such an adenovirus. The term "nucleic acid segment" refers to a polymer of DNA or RNA, i.e., a polynucleotide, which can be single- or double-stranded, and can optionally contain synthetic, nonnatural, or altered nucleotides. Any combination of such nucleotides can be incorporated into DNA or RNA polymers.

The term "substantially homologous" as used herein refers to the ability of two nucleic acids to hybridize under at least moderately stringent hybridization conditions. Stringency of hybridization is a term of art that refers to the conditions used for a hybridization reaction whereby complementary single strands of nucleic acid join to one another to form double-stranded nucleic acid with some degree of mismatch, the degree of which is a function of the stringency used. In particular, the stringency will depend upon the size and composition of the strands of nucleic acid that are caused to react, the degree of mismatching allowed, the desired cross reactivity, and the like. The degree of stringency can be affected by the ionic conditions employed and temperature, among others, as is well known in the art (Sambrook et al., *Molecular Cloning: A Laboratory Manual* (2d ed., 1989)).

As used in the context of the present invention, the specified stringency of hybridization in part defines the inventive nucleic acid. Accordingly, the hybridization conditions are designed suitably to be at least moderately stringent or stringent. In the former case, suitable conditions of salt, temperature, reaction mixture, and size of nucleic acid reactants are set in accordance with conventional knowledge to provide from about 45% to about 80% mismatch of the sequence of nucleotides of the nucleic acid. Preferably, moderately stringent hybridization conditions are set to provide from about 55% to about 75% mismatch; more preferably, such conditions are set to provide from about 60% to about 70% mismatch. In the latter case, suitable conditions for hybridization are set in accordance with conventional knowledge to provide from about 10% to about 40% mismatch. Preferably, stringent hybridization conditions are set to provide from about 20% to about 40% mismatch; more preferably, such conditions are set to provide from about 30% to about 40% mismatch. By mismatch, it is meant the degree to which non-complementary base pairs are found opposite one another in otherwise duplex nucleic acid, thereby forming bubble structures and causing the melting temperature of the duplex to be lower as compared to a 100% matched duplex of the same length and base composition.

The present inventive adenoviral vector preferably further comprises foreign nucleic acid, which will typically encode, and express within a host cell, a product that has therapeutic and/or prophylactic utility. The term "foreign nucleic acid" is used herein to refer to any sequence of DNA or RNA, particularly DNA, inserted into a vector of the present invention that is foreign to the adenoviral genome. Such foreign nucleic acid may constitute a gene, portion of a gene, or any other nucleic acid sequence, including but not limited to a sequence that encodes RNA, anti-sense RNA, a synthetic oligonucleotide, and/or a polypeptide. Foreign nucleic acids having therapeutic utility include genes that encode a missing or impaired gene function, such as the cystic fibrosis transmembrane regulator (CFTR) gene associated with cystic fibrosis (CF). Foreign nucleic acids having prophylactic utility include genes that encode a gene product that has an ability to prevent disease directly or indirectly, such as by providing a source of a polypeptide or other antigen to elicit an immune response thereto.

An adenovirus contains many regions. A region of the adenoviral genome comprises one or more genes (Horwitz, supra). Such genes encode gene products that mediate, facilitate, cause, or are the various components or activities of the adenovirus, such as attachment, penetration, uncoating, replication, core protein, hexon, fiber, hexon associated protein, and the like. One effect of a deficient region can be an inability of the adenovirus to propagate, for example, which may involve any or all of the aforementioned components or activities. The aforementioned components or activities are referred to herein as gene functions. A deficiency in a gene or gene function, i.e., a deficient gene, gene region, or region, as used herein is defined as a deletion of genetic material of the viral genome, which serves to impair or obliterate the function of the gene whose nucleic acid sequence was deleted in whole or in part and to provide room in or capacity of the viral genome for the insertion of a foreign nucleic acid. Such deficiencies can be in genes that are essential or unessential for propagation of the adenoviral vector in tissue culture in a noncomplementing cellular host.

The present inventive replication-deficient adenoviral vector can be deficient in any one or more regions, such as any region(s) in the early or late regions, required for viral replication. Preferably, the adenoviral vector of the present invention is deficient in at least one region of the early regions required for viral replication, particularly the E1 region, especially the E1A region alone or both the E1A and E1B regions. More preferably, the adenoviral vector is deficient in at least one region in addition to the deficiency in a region required for viral replication, e.g., deficient in an early region such as the E1A region in combination with a deficiency in another early region such as early region 1 (E1), including early region 1A (E1A) and/or early region 1B (E1B), early region 2 (E2), including early region 2A (E2A) and/or early region 2B (E2B), early region 3 (E3), and early region 4 (E4), or even a late region, of the adenoviral genome. While the deficiency of an additional region can be in a region not required for viral replication, such as the E3 region, the deficiency of an additional region can be desirably in another region required viral replication, although such an additional deficiency can be in conjunction with yet further deficiencies in region(s) which are or are not required for viral replication. Of particular interest are those adenoviral vectors of the present invention that can propagate in the HEK-293 cell line which has been previously utilized to supply the replication-essential E1 region to enable the propagation of E1-deficient group C adenoviral vectors.

Any one of the deleted regions can be replaced with a foreign nucleic acid such as a promoter-variable expression cassette to produce a foreign gene product, i.e., a gene product which is foreign with respect to the adenovirus. The insertion of a foreign nucleic acid into the E2A region, for example, can be facilitated by the introduction of a unique restriction site, such that the foreign nucleic acid product can be expressed by the E2A promoter.

The present invention is not limited to adenoviral vectors that are deficient in gene functions only in the early region of the genome. The present invention also includes those replication-deficient adenoviral vectors that are deficient in the late region of the genome, adenoviral vectors that are deficient in the early and late regions of the genome, as well as vectors in which essentially the entire genome has been removed, in which case it is preferred that at least the viral inverted terminal repeats and a packaging signal are left intact. One of ordinary skill in the art will appreciate that the larger the region of the adenoviral genome that is removed, the larger the piece of exogenous DNA that can e inserted into the genome. For example, given that the adenoviral genome is 36 kb, by leaving the viral inverted terminal repeats and some of the promoters intact, the capacity of the adenovirus is approximately 35 kb. Alternatively, one could generate an adenoviral vector that contains only the ITR and a packaging signal. This could then effectively allow for expression of 37–38 kb of foreign nucleic acid from the vector.

In general, virus vector construction relies on a high level of recombination between fragments of adenoviral DNA in the cell. Two or three fragments of adenoviral DNA, containing regions of similarity (or overlap) between fragments and constituting the entire length of the genome, are transfected into a cell. The host cell's recombination machinery constructs a viral vector genome by recombining the aforementioned fragments. Other suitable procedures for constructing viruses containing alterations in various single regions have been previously described (Berkner et al., *Nucleic Acids Res.*, 12, 925–941 (1984); Berkner et al., *Nucleic Acids Res.*, 11, 6003–6020 (1983); Brough et al., *Virol.*, 190, 624–634 (1992)) and can be used to construct multiply deficient viruses; further suitable procedures include, for example, in vitro recombination and ligation.

The initial step in virus vector construction is to construct a deletion or modification of a particular region of the adenoviral genome in a plasmid cassette using standard molecular biological techniques. This altered DNA (containing the deletion or modification) is then moved into a much larger plasmid that contains up to one half of the adenovirus genome. The next step is to transfect the plasmid DNA (containing the deletion or modification) and a large piece of the adenovirus genome into a recipient cell. Together these two pieces of DNA encompass all of the adenovirus genome plus a region of similarity. Within this region of similarity a recombination event will take place to generate a recombined viral genome that includes the deletion or modification. In the case of a replication-deficient vector, the recipient cell will provide not only the recombination functions but also all missing viral functions not contained within the transfected viral genome, thus complementing any deficiencies of the recombined viral genome and allowing for the propagation of the replication-deficient vector.

Preferably, the complementary cell line which allows for the propagation of a replication-deficient adenoviral vector of the present invention specifically complements for those functions that are missing from the replication-deficient adenoviral vector of interest. Such a cell line also preferably contains the complementing gene(s) in a nonoverlapping fashion so as to minimize, if not eliminate, the possibility of vector recombination yielding a replication-competent adenoviral vector.

The complementing cell line should be one that is capable of expressing the products of the deficient adenoviral gene functions necessary for replication at the appropriate level for those products in order to generate a high titer stock of recombinant adenoviral vector. For example, it is necessary to express the E2A product, DBP, at stoichiometric levels, i.e., relatively high levels, for adenoviral DNA replication, but the E2B product, Ad pol, is necessary at only catalytic levels, i.e., relatively low levels, for adenoviral DNA replication. Not only must the level of the product be appropriate, the temporal expression of the product must be consistent with that seen in normal viral infection of a cell to assure a high titer stock of recombinant adenoviral vector. For example, the components necessary for viral DNA replication must be expressed before those necessary for virion assembly. In order to avoid cellular toxicity, which often accompanies high levels of expression of the viral products, and to regulate the temporal expression of the products, inducible promoter systems are used. For example, the sheep metallothionine inducible promoter system can be used to express the complete E4 region, the open reading frame 6 of the E4 region, and the E2A region. Other examples of suitable inducible promoter systems include, but are not limited to, the bacterial lac operon, the tetracycline operon, the T7 polymerase system, and combinations and chimeric constructs of eukaryotic and prokaryotic transcription factors, repressors and other components. If the viral product to be expressed is highly toxic, it is desirable to use a bipartite inducible system, wherein the inducer is carried in a viral vector and the inducible product is carried within the chromatin of the complementing cell line. Repressible/inducible expression systems, such as the tetracycline expression system and lac expression system, also can be used.

DNA that enters a small proportion of transfected cells can become stably maintained in a few such cells. The isolation of a cell line that expresses one or more transfected genes is achieved by introduction into the same cell of a second gene (marker gene) that, for example, confers resistance to an antibiotic, drug or other compound. This selection is based on the fact that, in the presence of the antibiotic, drug, or other compound, the cell without the transferred gene dies, while the cell containing the transferred gene survives. The surviving cells are then clonally isolated and expanded as individual cell lines. Within these cell lines are those that express both the marker gene and the gene or genes of interest. Propagation of the cells is dependent on the parental cell line and the method of selection. Transfection of the cell is also dependent on cell type. The most common techniques used for transfection are calcium phosphate precipitation, liposome, or DEAE dextran mediated DNA transfer.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of a given gene and can be constructed by conventional synthetic or site-specific mutagenesis procedures. Synthetic DNA methods can be carried out in substantial accordance with the procedures of Itakura et al., *Science*, 198, 1056 (1977), and Crea et al., *Proc. Natl. Acad. Sci. USA*, 75, 5765 (1978). Site-specific mutagenesis procedures are described in Maniatis et al., *Molecular Cloning: A Laboratory Manual*, Cold Spring Harbor, N.Y. (2d ed. 1989). Therefore, the present invention is in no way limited to the DNA sequences and plasmids specifically exemplified herein. Exemplified vectors are for the marker gene chloramphenicol acetyl transferase (CAT), and for the gene therapy of cystic fibrosis; therefore, the particular vectors described herein contain and express the CAT gene and the cystic fibrosis transmembrane regulator (CFTR) gene. The vectors described herein, however, are easily convertible to treat various diseases including, but not limited to, other chronic lung diseases, such as emphysema, asthma, adult respiratory distress syndrome, and chronic bronchitis, as well as cancer, coronary heart disease, and other afflictions suitably treated or prevented by gene therapy, vaccination, and the like. Accordingly, any gene or DNA sequence can be inserted into a non-group C adenoviral gene transfer vector. The choice of gene or DNA sequence is one that achieves a therapeutic and/or prophylactic effect, for example, in the context of gene therapy, vaccination, and the like.

One skilled in the art will appreciate that suitable methods of administering an adenoviral vector of the present invention to an animal for therapeutic or prophylactic purposes, e.g., gene therapy, vaccination, and the like (see, for example, Rosenfeld et al., *Science*, 252, 431–434 (1991); Jaffe et al., *Clin. Res.*, 39(2), 302A (1991); Rosenfeld et al., *Clin. Res.*, 39(2), 311A (1991); Berkner, *BioTechniques*, 6, 616–629 (1988)), are available, and, although more than one route can be used to administer the vector, a particular route can provide a more immediate and more effective reaction than another route. Pharmaceutically acceptable excipients are also well-known to those who are skilled in the art, and are readily available. The choice of excipient will be determined in part by the particular method used to administer the composition. Accordingly, there is a wide variety of suitable formulations of the pharmaceutical composition of the present invention. The following formulations and methods are merely exemplary and are in no way limiting, although oral, injectable, and aerosol formulations are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The vectors of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the vectors employed in the present invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene or other sequence of interest, the composition employed, the method of administration, and the particular site and organism being treated. The dose should be sufficient to effect a desirable response, e.g., therapeutic or prophylactic response, within a desirable time frame.

The non-group C adenoviral gene transfer vectors of the present invention also have utility in vitro. For example, they can be used to study adenoviral gene function and assembly with respect to the adenoviruses of the various groups. Alternatively, one can study expression of foreign nucleic acid in a suitable target cell using the vectors of the present invention. One of ordinary skill can identify a suitable target cell by selecting one that can be transfected by the inventive adenoviral vector and/or infected by adenoviral particles, resulting in expression of the thereby inserted adenoviral DNA complement. Preferably, a suitable target cell is selected that has receptors for attachment and penetration of adenovirus into a cell. Such cells include, but are not limited to, those originally isolated from any mammal. Once the suitable target cell has been selected, the target cell is contacted with a foreign nucleic acid-containing recombinant adenoviral vector or adenoviral particle of the present invention, thereby effecting transfection or infection, respectively. Expression, toxicity, and other parameters relating to the insertion and activity of the foreign nucleic acid in the target cell is then measured using conventional methods well known in the art. In so doing, researchers can learn and elucidate the phenomenology concerning adenoviral infection as well as the efficacy and effect of expression of various sequences of foreign nucleic acid introduced by the inventive vector in various cell types that are explanted from various organisms and studied in tissue culture.

Moreover, cells explanted or removed from a patient having a disease that is suitably treated by gene therapy in the context of the present invention usefully are manipulated in vitro. For example, cells cultured in vitro from such an individual are placed in contact with an adenoviral vector of the present invention under suitable conditions to effect transfection, which are readily determined by one of ordinary skill in the art, where the vector includes a suitable foreign nucleic acid. Such contact suitably results in transfection of the vector into the cultured cells, where the transfected cells are selected for using a suitable marker and selective culturing conditions. In so doing, using standard methods to test for the vitality of the cells and thus measure toxicity and to test for the presence of gene products of the foreign nucleic acid of the vector of interest and thus measure expression, the cells of the individual are tested for compatibility with, expression in, and toxicity of the foreign nucleic acid-containing vector of interest, thereby providing information as to the appropriateness and efficacy of treatment of the individual with the vector/foreign nucleic acid system so tested. Such explanted and transfected cells, in addition to serving to test the potential efficacy/toxicity of a given gene therapy regime, can be also returned to an in vivo position within the body of the individual. Such cells so returned to the individual can be returned unaltered and unadorned except for the in vitro transfection thereof, or encased by or embedded in a matrix that keeps them separate from other tissues and cells of the individual's body. Such a matrix can be any suitable biocompatible material, including collagen, cellulose, and the like. Of course, alternatively or in addition, once having observed a positive response to the in vitro test, the transfection can be implemented in situ by administration means as detailed hereinabove.

The following examples further illustrate the present invention and, of course, should not be construed as in any way limiting its scope. Enzymes referred to in the examples are available, unless otherwise indicated, from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250, and are used in substantial accordance with the manufacturer's recommendations. Many of the techniques employed herein are well known to those in the art. Molecular biology techniques are described in detail in suitable laboratory manuals, such as Sambrook et al., *Molecular Cloning: A Laboratory Manual*, Cold Spring Harbor, N.Y. (2d ed. 1989), and *Current Protocols in Molecular Biology* (Ausubel et al., eds. (1987)). One of ordinary skill in the art will recognize that alternate procedures can be substituted for the various procedures presented below.

EXAMPLE 1

This example illustrates the deletion of the E1A region from the adenoviral DNA of Ad7a virus of group B, thereby generating viral large fragments.

Ad7a virus was used to inoculate HEK-293 cells in modified Eagle's medium with 5% horse serum at 100 multiplicity of infection, and the DNA was isolated from harvested Ad7a virus, using the methods described in Falck-Pedersen, in *Cell Biology: A Laboratory Manual* (Spector et al., eds., Cold Spring Harbor Laboratory, New York, 1994). Ad7a DNA was then subjected to restriction endonuclease cleavage with Aat II according to Dijkema et al., *Gene*, 12, 287 (1980), thereby producing a 1.483 kb small fragment of the left hand (fragment 1 in FIG. 1A), a large fragment of approximately 30 kb located in the center of the genome (fragment 2 in FIG. 1A), and a second large fragment of 5 kb of the right hand (fragment 3 in FIG. 1A). The small fragment includes the origin of replication and packaging sequences as well as early region E1A, which is necessary for DNA replication. The large fragments contain the other early genes as well as the late genes required for production of new virions.

Figure 1B:
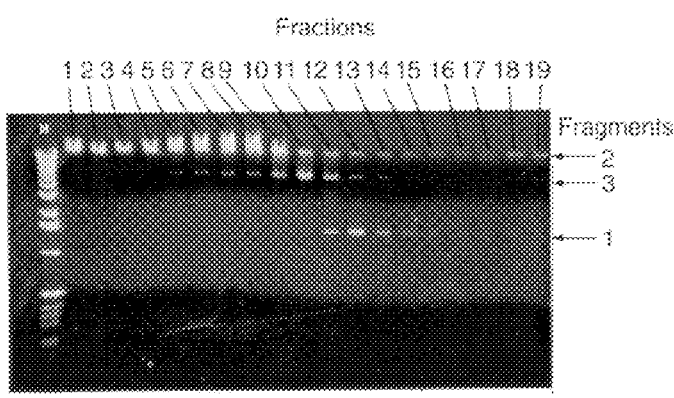
FIG. 1B is a scanned image of a stained gel electrophoresis assay of the fractions of a sucrose gradient used to separate the AatII restriction fragments of Ad7 DNA.

Large fragments 2 and 3 were copurified and isolated separately from the small fragment by sucrose density gradient centrifugation. A 10% to 20% continuous sucrose gradient with a 40% sucrose cushion was overlayed with Aat II digested Ad7a DNA. Following centrifugation, the gradient was fractionated. Fractions containing purified large fragments were determined by agarose gel electrophoresis; a scanned image of the ethidium bromide stained gel appears in FIG. 1B. Fractions 1–10 include no detectable small fragments.

Figure 1C:
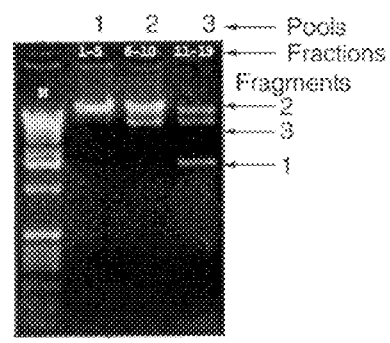
FIG. 1C is a second scanned image of a stained gel electrophoresis assay of the pooled and concentrated fractions of the same sucrose gradient separated restriction fragments.

Fractions 1–5, 6–10, and 11–19 were pooled and concentrated by precipitation and subsequent reconstitution in a smaller volume. Gel electrophoresis was used again to analyze the size of the DNA fragments in each of the pooled fractions, the results of which are shown in FIG. 1C. Pool 2 (fractions 6–10) was used in subsequent steps in the preparation of the Ad7a replication-deficient virus because of the presence of the large fragments (2 and 3) and the absence of the small fragment (1), which was known to include region E1A.

EXAMPLE 2

Figure 2:
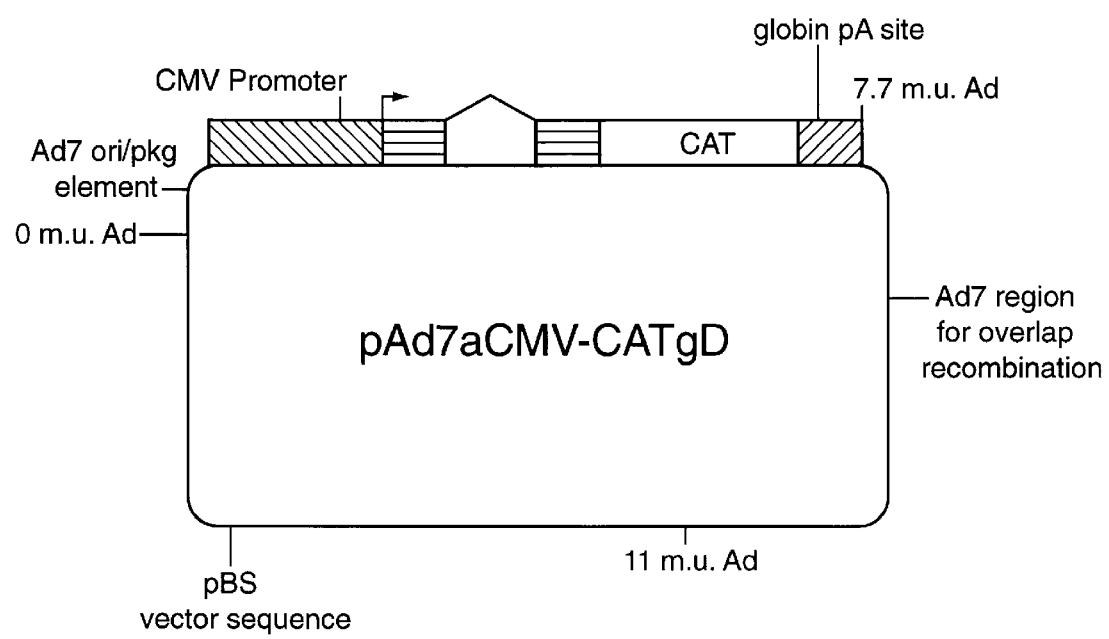
FIG. 2 is a schematic diagram of the pAd7aCMV-CATgD plasmid.

This example describes the generation of the plasmid pAd7aCMV-CATgD, which is depicted in FIG. 2. The plasmid pAd7aCMV-CATgD was prepared by directional cloning in three sequential steps.

First, using oligonucleotide primers and the polymerase chain reaction (PCR), up to 475 base pairs of the left end of the Ad7a genome (located between 0 and 1.3 map units (mu) on the Ad7a genome) were amplified and isolated. The primers used were:

GAGCTC-ACCGGT-CTCTCTATATAATATACC [SEQ ID NO:1]
  |        |         |
 SaCI     AgeI    1–18 bp Ad7

TCTAGA-GCGGCCGC-AGCGATCAGCTGACACCTACG [SEQ ID NO:2]
  |        |              |
 XbaI     NotI       475–455 bp Ad7

The amplified DNA contained the essential origin (ori) and packaging sequences (pkg). The early regions E1A and a portion of E1B, located between 1.3 and 7.7 mu, were thereby deleted. The pBS vector (Stratagene Cloning Systems, La Jolla, CA) was then opened with SacI-NotI, and the PCR fragment SacI-ori/pkg-NotI was inserted therein.

Second, using standard methods, the pBS vector was opened with NotI-SalI, and the cytomegalovirus promoter (CMV) was ligated to the ori and pkg elements, followed by the bacterial chloramphenicol acetyl transferase sequence (CAT) and the mouse B-maj globin poly (A) site.

Third, a region of 2.8 to 4.0 kb for overlap recombination with the Ad7a genome was generated by PCR using the following primers:

GCTAGC-GTCGAC-GAAGAAATGCATGTTTG [SEQ ID NO:3]
  |        |          |
 NheI     SalI    2800–2816 bp Ad7

GGGCCC-GGTACC-CAATGATCGAAACCG [SEQ ID NO:4]
  |        |          |
 ApaI     KpnI    4000–3986 bp Ad7

This overlap recombination fragment is located at 7.7 to 11.1 mu on the Ad7a genome. The pBS vector was then opened with SalI-KpnI, and the PCR fragment SalI-Ad7 overlap DNA 2.8–4.0 kb-KpnI was inserted therein, i.e., ligated to the aforementioned DNA construct after the poly (A) site, thus resulting in the generation of the pAd7aCMV-CATgD plasmid.

EXAMPLE 3

This example describes the generation of recombinant Ad7a adenovirus and demonstrates the ability of the recombinant Ad7a adenovirus to be replicated in and complemented by HEK-293 cells.

Various ratios of micrograms of viral large fragments prepared in accordance with Example 1 and plasmid pAd7aCMV-CATgD prepared in accordance with Example 2 were transfected onto monolayers of HEK-293 cells ($10^6$ cells per 60 mm dish) by calcium phosphate precipitation. After one week, the cells were harvested, and a virus lysate was generated by repeat freeze-thaw cycles. A 10% portion of the resulting lysate (0.5 ml) was used to infect a fresh monolayer of HEK-293 cells. After 24 hours, these cells were harvested and lysates prepared. The lysates were tested for reporter gene activity, i.e., chloramphenicol acetyl transferase (CAT) activity, using the method disclosed in Gorman et al., *Mol. Cell Biol.*, 2, 1044–1051 (1982), and Gorman et al., *PNAS*, 79, 6777–6781 (1982).

Figure 3:
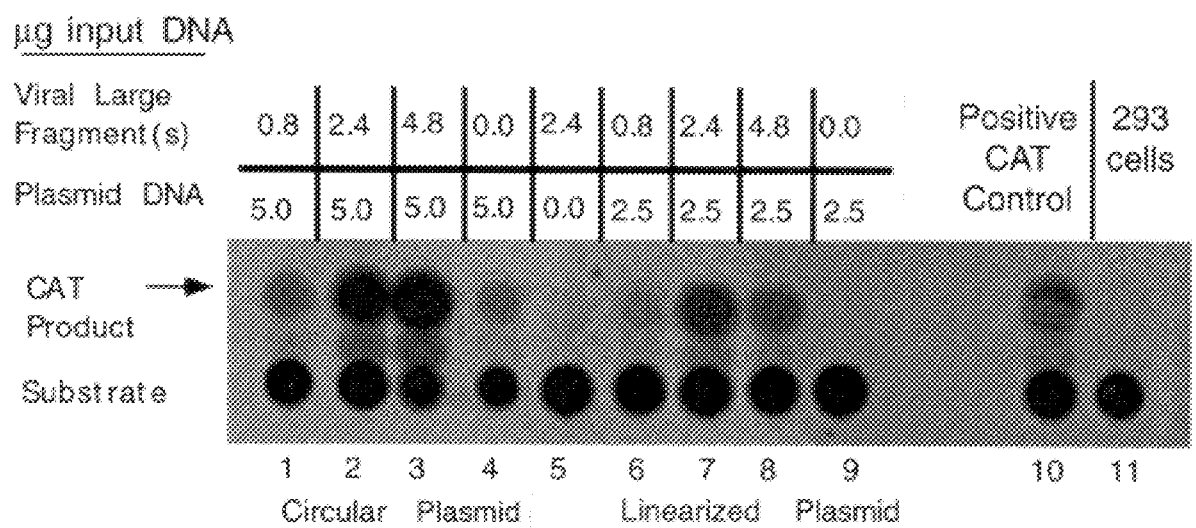
FIG. 3 is a scanned image of an assay of chloramphenicol acetyl transferase activity in aliquots of lysates of HEK-293 cells after transfection, which was conducted using varying combinations of viral large fragments and plasmid DNA.

The results of the transfections using circular and linearized plasmid are shown in FIG. 3, which is a dot blot where the generated color is more intense in the presence of higher CAT concentrations. The combination of 2.4–4.8 μg of large viral fragment and 5.0 μg of circular plasmid produced the highest CAT activity in resultant lysates (see lanes 2 and 3). With respect to linearized plasmid, the combination of 2.4 μg of large fragment and 2.5 μg of plasmid (lane 7) produced the best result. Positive and negative controls are located in lanes 10 and 11, respectively.

EXAMPLE 4

This example further confirms the generation of recombinant Ad7a adenovirus and the ability of the recombinant Ad7a adenovirus to be replicated in and complemented by HEK-293 cells. In particular, this example describes the test of a secondary virus lysate for CAT gene expression.

A 1.0 ml aliquot of the primary lysate generated in accordance with Example 3 was used to infect a 60 mm dish of HEK-293 cells. After incubation for one week, the cells were harvested, and lysates were generated, as in Example 3. A 10% portion of each lysate was then used to infect a fresh monolayer of HEK-293 cells, and the resultant lysate thereof was tested for CAT activity.

Figure 4A:
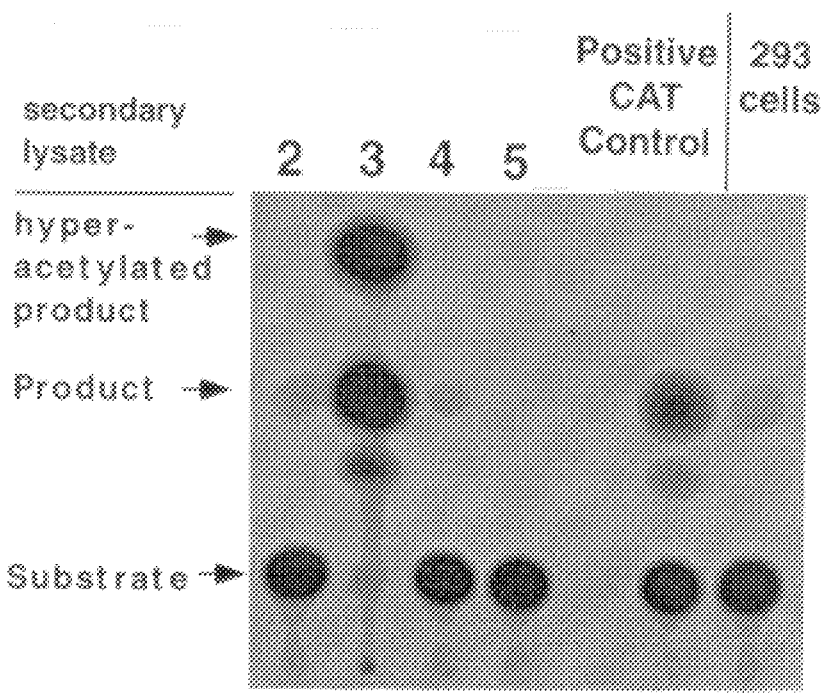
FIG. 4A is a scanned image of an assay of chloramphenicol acetyl transferase activity in aliquots of secondary virus lysates of HEK-293 cells after infection.

The results are depicted in FIG. 4A. The lysate number indicates the transfection parameters, which were the same as those of the corresponding numbers in FIG. 3. The results show that the transfection parameter of 4.8 μg of large fragment combined with a nearly equal mass of circular plasmid (i.e., 5 μg) results in strong CAT activity in a secondary lysate, that is the result of the viral activity of the progeny of the initially harvested recombinant virus particles.

Figure 4B:
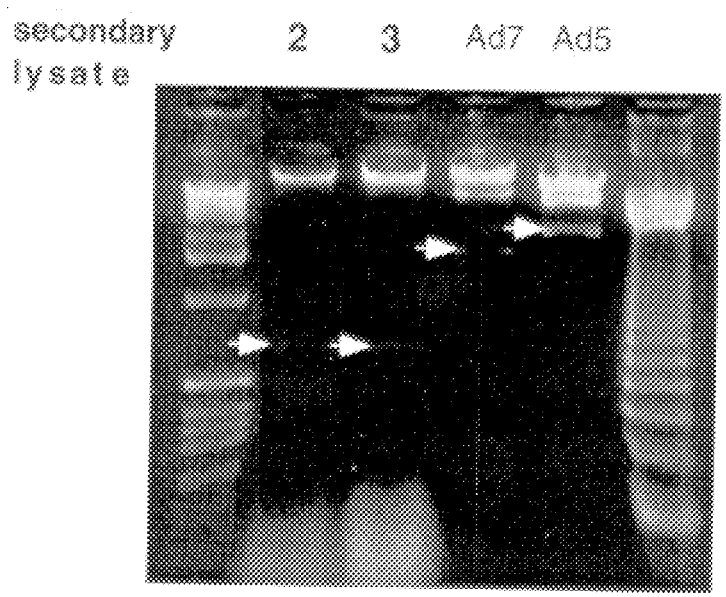
FIG. 4B is a scanned image of gel separated and stained AatII restriction endonuclease fragments of the DNA taken from the same lysates.

Selected cell lysates (2 and 3) were further characterized by infecting HEK-293 cells and harvesting viral DNA by a modified Hirt procedure (Falck-Pedersen, supra). Viral DNA purified in this manner was digested by the restriction endonuclease AatII in order to characterize the nature of the recombinant DNA, as depicted in FIG. 4B. Control DNA was taken from wild-type Ad7a and wild-type Ad5 adenoviruses. Diagnostic bands are highlighted by arrows. Lanes 2 and 3 each have the same smaller DNA AatII restriction fragment, as compared to the indicated AatII restriction fragments in the control Ad7 and Ad5 lanes. Accordingly, the CAT activity of the recombinant Ad7a treated lysates correlates, as expected, to a genetic alteration.

EXAMPLE 5

This example evaluates the similarities between non-group C adenoviruses with respect to group C adenoviruses.

The similarities and differences between various adenovirus groups were examined by comparing the amino acid similarity and identity between the E1A and E1B gene products of Ad2 (group C), Ad5 (group C), Ad7 (group B), Ad12 (group A), and Ad40 (group F) adenoviruses. As regards viruses within the same group, specifically as between Ad2 and Ad5 within group C, there was 99% similarity and 98% identity between the E1A and E1B gene products of Ad2 and Ad5. In contrast, comparisons between the viruses of the different groups revealed a greatly reduced similarity and less identity. For example, there was 63–75% similarity and 40–53% identity between the E1A and E1B gene products of Ad7, Ad12, and Ad40 as compared with the E1A and E1B gene products of Ad2 and Ad5.

Significantly, however, particular domains were found to be conserved among the viruses of the different groups, e.g., as between the non-group C and group C adenovirus E1A and E1B gene products. Thus, the differences between particular non-group C viruses as compared to group C viruses were found to be similar, such that, for example, the demonstration of an ability of group B adenoviruses is indicative of the same ability being possessed by other non-group C adenoviruses. In particular, the demonstration of the ability of an E1-defective group B adenovirus, e.g., Ad7, to be complemented by HEK-293 cells (as demonstrated in Example 3) evidences the ability of other non-group C adenoviruses to be complemented by HEK-293 cells.

All references, including publications and patents, cited herein are hereby incorporated by reference to the same extent as if each reference were individually and specifically indicated to be incorporated by reference and were set forth in its entirety herein.

While this invention has been described with an emphasis upon preferred embodiments, it will be apparent to those of ordinary skill in the art that the preferred embodiments can be varied. Similarly, it is intended that the invention can be practiced otherwise than as specifically described herein. Accordingly, this invention includes all modifications encompassed within the spirit and scope of the appended claims.

What is claimed is:

1. A stock of a replication deficient adenoviral gene transfer vector, said vector comprising (a) an expression cassette that encodes a foreign gene product, and (b) an adenoviral DNA segment isolated from an adenovirus selected from the group consisting of A, B, D, E and F adenovirus, wherein said vector stock is free of replication competent adenovirus.

2. The vector stock of claim 1, wherein said vector is deficient in at least the E1A region of the adenoviral genome.

3. The vector stock of claim 2, wherein said adenovirus is a group B adenovirus.

4. The vector stock of claim 3, wherein said adenovirus is an Ad7 adenovirus.

5. The vector stock of claim 2, wherein said vector replicates in the HEK-293 cell line.

6. The vector stock of claim 2, wherein said vector is further deficient in at least another region of the adenoviral genome.

7. The vector stock of claim 2, wherein said vector is further deficient in at least another region of the adenoviral genome required for viral replication.

8. The vector stock of claim 2, wherein said vector is further deficient in a region selected from the group consisting of the E1B, E2, E3, and E4 regions of the adenoviral genome.

9. The vector stock of claim 2, wherein said vector is further deficient in a region selected from the group consisting of the late regions of the adenoviral genome.

10. A method of testing the expression of a foreign gene product upon transfection into an isolated target cell, which method comprises (a) selecting a target cell, (b) contacting said target cell with the vector stock of claim 1, and (c) determining the expression of said foreign gene product in said isolated target cell.

11. The vector stock of claim 2, wherein said stock is propagated in a cell line that complements in trans a group C adenovirus deficient in the E1A region of the adenoviral genome.

12. The vector stock of claim 11, wherein said cell line is an HEK-293 cell line.

13. A method of growing and propagating an isolated non-group C adenoviral vector stock in the absence of a helper virus which method comprises contacting a cell of a cell line that is capable of complementing the replication of a group C adenovirus that is deficient in at least the E1A region of the adenoviral genome with a non-group C adenovirus deficient in at least the E1A region of the adenoviral genome.

14. The method of claim 13, wherein said cell line is an HEK-293 cell line.

15. The method of claim 13, wherein said vector is further deficient in another region of the adenoviral genome.

16. The method of claim 13, wherein said non-group C vector is of group B.

17. The method of claim 16, wherein said group B vector is an Ad7 adenovirus.

* * * * *